United States Patent [19]

Scott et al.

[11] Patent Number: 5,073,345

[45] Date of Patent: Dec. 17, 1991

[54] LIGHT DETECTOR APPARATUS

[75] Inventors: Raymond P. W. Scott, Wilton; Gary J. Schmidt, New Fairfield, both of Conn.

[73] Assignee: The Perkin Elmer Corporation, Norwalk, Conn.

[21] Appl. No.: 753,370

[22] Filed: Jul. 9, 1985

Related U.S. Application Data

[63] Continuation of Ser. No. 499,702, May 31, 1983.

[51] Int. Cl.$^5$ .................... G01N 21/01; G01N 30/02
[52] U.S. Cl. .................... 422/70; 73/61.1 C; 356/246; 356/410; 356/411; 356/436; 422/82.09; 436/161
[58] Field of Search .................... 73/61.1 C; 356/411, 356/410, 436, 246; 422/68, 70, 82.09; 436/161

[56] References Cited

U.S. PATENT DOCUMENTS

| | | | |
|---|---|---|---|
| 3,544,798 | 12/1970 | Topol | 356/411 X |
| 3,614,242 | 10/1971 | Hrdina | 356/410 |
| 3,630,681 | 12/1971 | Arikawa | 422/70 X |
| 3,711,206 | 1/1973 | Moran | 356/246 X |
| 3,861,802 | 1/1975 | Belmear | 356/410 X |
| 3,962,041 | 6/1976 | Muller et al. | 435/291 |
| 3,970,388 | 7/1976 | Hacker | 356/436 X |
| 3,994,590 | 11/1976 | Di Martini et al. | 356/409 X |
| 4,233,030 | 11/1980 | Twitchett et al. | 422/70 X |
| 4,330,206 | 5/1982 | Gausmann et al. | 356/246 |
| 4,374,620 | 2/1983 | Berick et al. | 356/246 |
| 4,414,842 | 11/1983 | Small et al. | 73/61.1 C |
| 4,462,962 | 7/1984 | Baba et al. | 422/58 |

OTHER PUBLICATIONS

Ersser et al., Modular Apparatus for the Automation of Ion-Exchange Column Chromatographic Procedures, Laboratory Practice, vol. 24, No. 11, pp. 741-743.
H. Small, T. S. Stevens, W. C. Bauman, "Novel Ion Exchange Chromatographic . . . ", Analytical Chemistry, vol. 47, No. 11, Sep. 1975, pp. 1801-1809.
S. Elchuck & R. M. Cassidy, "Separation of the Lanthanides . . . ", Analytical Chemistry, vol. 51, No. 9, Aug. 1979, pp. 1434-1438.
R. M. Cassidy & S. Elchuck, "Dynamically Coated Column . . . ", Analytical Chemistry, vol. 54, pp. 1558-1563.
E. D. Katz & R. P. W. Scott, "Low Dispersion Connecting Tubes . . . ", Journal of Chromatography, 268 (1983), pp. 169-175.
R. P. W. Scott & P. Kucera, "Examination of Five Commercially Available . . . ", Journal of Chromatography, 142 (1977), pp. 213-232.
R. P. W. Scott, "Contemporary Liquid Chromatography", (1976), pp. 138-141.

*Primary Examiner*—Jill Johnston
*Attorney, Agent, or Firm*—Edwin T. Grimes; Thomas P. Murphy

[57] ABSTRACT

A light absorption detector includes a light source substantially adjacent a window of a chromatogrpahic flow cell. The flow cell is defined by a housing member which also includes a photo-sensitive detector.

4 Claims, 2 Drawing Sheets

| METAL | ABSORPTION MAXIMA (nm) | SENSITIVITY (g/mL) |
|---|---|---|
| Cu | 507 | $3.2 \times 10^{-7}$ |
| Pb | 498 | $4.7 \times 10^{-8}$ |
| Zn | 489 | $7.9 \times 10^{-8}$ |
| Ni | 499 | $2.3 \times 10^{-7}$ |
| Co | 506 | $5.4 \times 10^{-9}$ |
| Cd | 485 | $1.0 \times 10^{-8}$ |
| Fe | 481 | $2.4 \times 10^{-8}$ |
| Mn | 491 | $3.3 \times 10^{-8}$ |

LIGHT DETECTOR APPARATUS

This application is a continuation of application Ser. No. 499,702, filed May 31, 1985, and not abandoned.

BACKGROUND OF THE INVENTION

The present invention generally relates to a light detector apparatus and, in particular, relates to such a detector apparatus adaptable for use in ion chromatography.

In general, liquid chromatography is an analytical technique which frequently employs light absorption detectors to determine the presence or absence of a material in the eluent of a chromatographic separating column. Such detectors ordinarily are quite expensive due to the necessary optical elements required. For example, such a detector can often include such elements as a scanning monochromator, numerous lenses and mirrors as well as a rather expensive light source. In addition, such an apparatus is usually required to be clean, stable and aligned.

One application of liquid chromatography, however, does not ordinarily employ a light absorption detector. This application is generally referred to as ion chromatography and, because of the ionic nature of the analytes, usually employs a conductivity detector. Due to its multielement capability, the use of ion chromatography is attractive for the direct determination of metals in a variety of sample matrices.

However, one limitation of the application of ion chromatography to metals is the lack of specificity of the conductivity detector. Present conductivity detectors often cannot distinguish a small conductivity change due to the element of interest because it is superpositioned on a high conductivity mobile phase. Consequently, a weakly conducting solvent material has been required in order to be able to distinguish the presence of a metal therein. However, the use of such weak mobile solvents restricts the flexibility of the chromatographic system since high conductivity mobile phases are excluded.

SUMMARY INVENTION

Accordingly, it is one object of the present invention to provide a detector apparatus which is adaptable for use in ion chromatography.

This object is achieved, at least in part, by a light absorption detector including a housing defining a flow cell, having an optical window adjacent one end of the cell and having a light source optically adjacent the window.

Other objects and advantages will become apparent to those skilled in the art from the following detailed descriptions read in conjunction with the appended claims and the drawings attached hereto.

BRIEF DESCRIPTION OF THE DRAWING

The drawing, not drawn to scale, embodying the principles of the present invention includes.

DETAILED DESCRIPTION OF THE INVENTION

Figure 1:
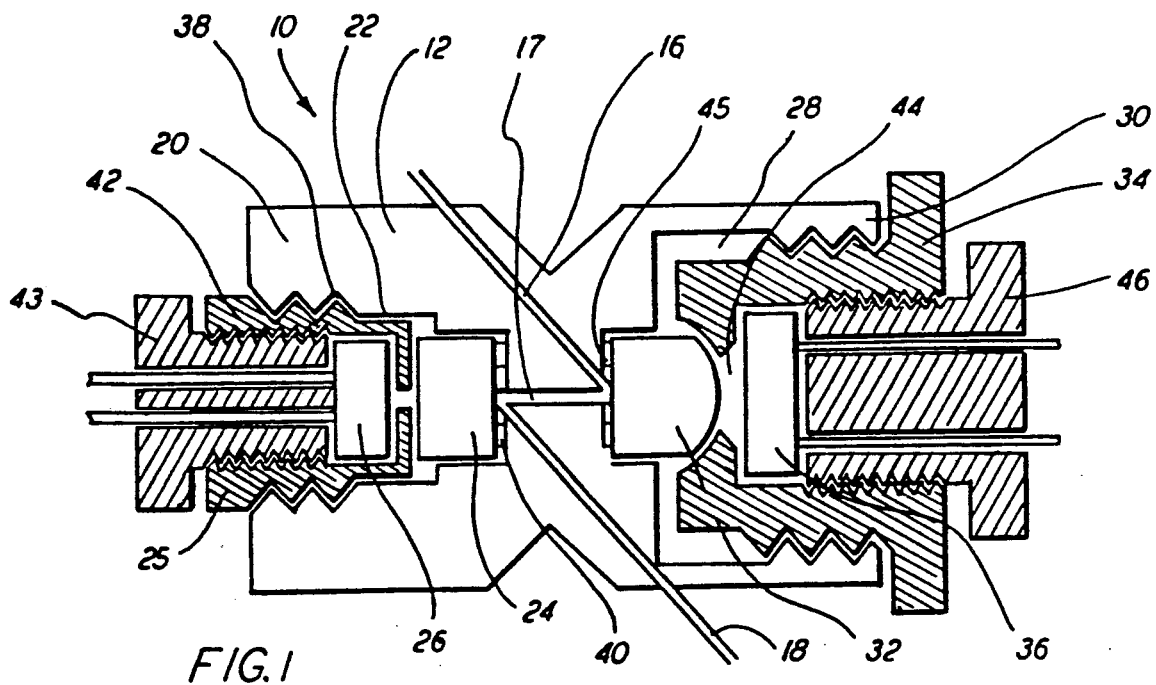
FIG. 1 is a partial cross-section view of a detector apparatus embodying the principles of the present invention.

A light absorption detector, generally indicated at numeral 10 and embodying the principles of the present invention, includes a housing member 12 which housing member defines a liquid chromatography flow cell 17 therein, including inlet and outlet fluid communication means 18 and 16, respectively. One end 20 of the housing 12 includes a first cavity 22 wherein a first quartz window 24 is sealingly adjacent one end 20 of the flow cell 17. Preferably the first quartz window 24 is held in position by a first retaining means 25. Further, a light source 26 is rigidly, but removably, positioned, optically adjacent to the first window 24. As used herein the phrase 'optically adjacent' is meant to define the relationship between two elements which are, for all intents and purposes, adjacent to each other and includes the condition wherein no optical element lies between the two.

The housing member 12 also includes a second cavity 28 in the opposing end 30 thereof in which second cavity 28 is positioned a second quartz window 32 which is secured in place by a second retaining means 34. The second retaining means 34 is adapted to contain therein a photo-sensitive detector 36. The photo-sensitive detector 36 is rigidly, but removably, positioned within the second retaining means 34.

Figures 3, 4:
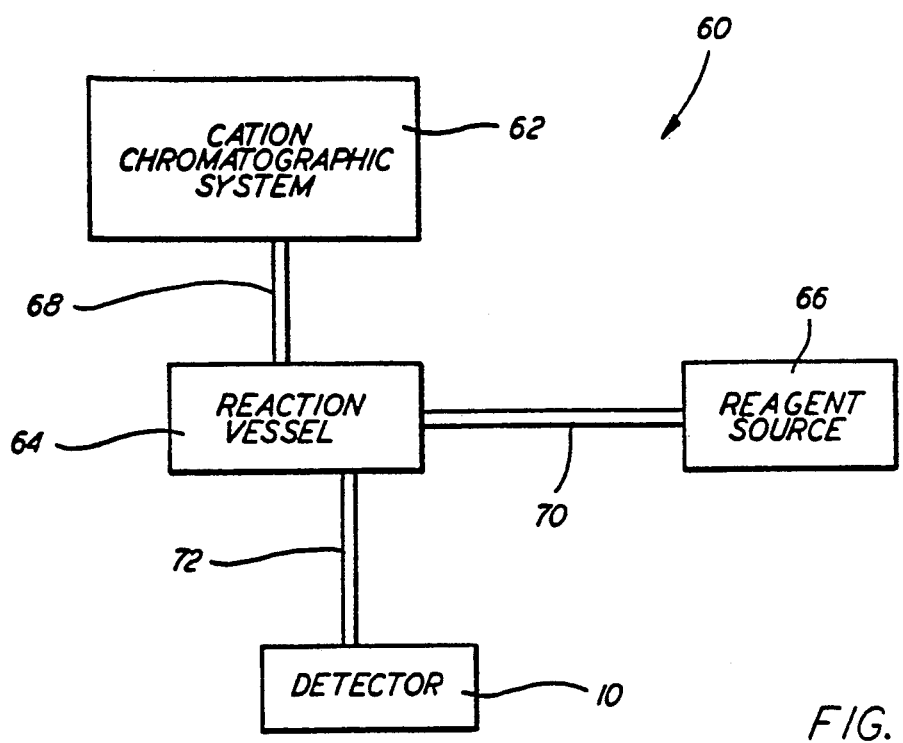
FIG. 3 is a block diagram of a chromatography system employing the apparatus of the present invention.
FIG. 4 is a tabulation of measured data.

In the preferred embodiment the housing member 12 is formed from a stainless steel member having an outside diameter on the order of about 17 mm and having a 0.74 mm opening through the center portion thereof. The housing member 12 includes inlet means 18 whereby an effluent from a reaction vessel, shown in FIG. 3, is provided to the flow cell 17. In the preferred embodiment, the inlet means 18 is on the order of about 0.25 mm diameter and intersects the flow cell 17 at the light source side at approximately 45°. The outlet means 16, preferably intersecting the other end of the flow cell 17, has a diameter on the order of about 0.5 mm. Preferably, to minimize the unswept volume within the flow cell 17, the inlet and outlet means 18 and 16 respectively, are substantially parallel to each other. The flow cell 17 has a volume of approximately 1.7 microliters.

The first cavity 22 provided in the one end 20 of the housing member 12 is preferably provided with internal threads 38 and is cooperatively sized to accept the first quartz window 24 therein. The first quartz window 24 preferably has an outside diameter of about 4.5 mm and a thickness on the order of about 3 mm. In one embodiment the quartz window 24, is sealed against the one end of the flow cell 17 via, for example, a neoprene washer 40 and in position via an externally threaded gland nut 42. As more fully explained below the use of a neoprene washer 40 is warrented herein since most solutions for which the detector 10 is designed to operate are aqueous solutions and therefore do not normally cause deterioration of the seal.

In the preferred embodiment, the light source 26 is an LED such as that marketed by Radio Shack and designated as part number 276-034. The LED is positioned within the retaining means 42 of the first quartz window 24 by, for example, an externally threaded gland nut 43. By this arrangement, there is little or no stray light available to pass through the first quartz window 24.

On the other end 30 of the housing 12, within the second cavity 28, the second quartz window 32 is sealingly affixed, via, for example, another neoprene washer 45 and the second retaining means 34. In the preferred embodiment, the end of the second quartz window 32 distal the flow cell 17 is rounded so as to diffuse light passing therethrough across a larger area of the photo-sensitive detector 36.

The photo-sensitive detector 36 is positioned within a cavity 44 extending into the second retaining means 34 and secured in place by means of, for example, a gland nut 46. The detector 36 can be a photo diode such as a S1336-5BQ-2L marketed by HAMAMATZU INC.

Figure 2:
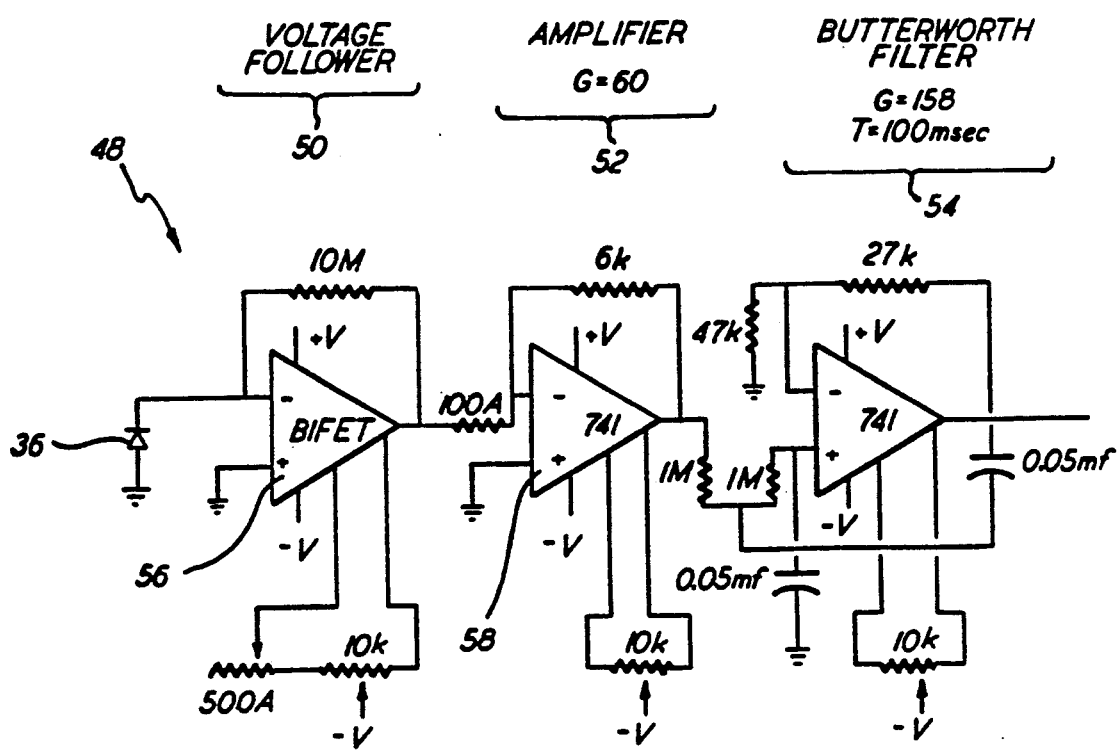
FIG. 2 is an exemplary circuit schematic for the detector apparatus.

Referring specifically to FIG. 2 an electronic circuit 48 for the output of the detector is shown in schematic form. However, any circuitry capable of producing an indication responsive to such a photo-diode is acceptable. One exemplary embodiment includes a tri-sectional circuit. That is, the photo-diode is connected directly to a voltage follower stage 50, which then drives an amplifier stage 52 which is followed by a Butterworth filter 54.

The voltage follower 50 converts the current from the photo-diode from a high impedance to a low impedance and incorporates a BIFET operational amplifier 56. The signal therefrom is amplified by the amplifier stage 52. In the embodiment shown the amplifier stage 52 utilizes an operational amplifier 58, such as a UA741CP, which produces a gain of about 60. The 1.8 cycle, second order Butterworth filter 54 follows the amplifier 56 to reduce the noise of the signal. The output of the filter 54 can be provided to any desired display or recording device.

One primary advantage of the detector 10 described herein is that it is extremely compact, i.e., having an total length of about 23 millimeters. Further, since the light source 26 is effectively adjacent the entrance window of the flow cell 17, all light passing into the flow cell 14 is generated by the source 26 and therefore there is little extraneous or scattered light entering the flow cell 17. Additionally, since this detector, 10 is preferably used as a dedicated detector for cation chromatography, there are no moving optical elements, nor are there any active optical elements.

The preferred embodiment of the above-described detector apparatus 10 was used to determine the linearity and detection limits for a number of different cations of metals. The minimum detectable concentration was taken as equivalent to the concentration calculated to produce a signal equal to twice the noise level of the system.

An experimental arrangement 60 is shown in FIG. 3 and includes a conventional cation chromatographic system 62, a reaction vessel 64, a source of reagent 66 and the light detector apparatus 10. As shown, the effluent of the cation chromatographic system 62 is provided to the reaction vessel 64 via a conduit 68. A reagent is also provided to the vessel 64 via conduit 70. The reactant is then provided to the inlet means 16 of the detector apparatus 10 via conduit 72.

The experiments performed included the use of 4-(2-pyridylaza) resorcinol as a reagent and such use ensured that the resultant reacted material would absorb light at a wavelength close to the peak wavelength output of the selected light source.

In utilizing the present detector apparatus 10, the selection of the reagent with which eluted cations react is dictated to some degree by the wavelength at which it absorbs light. Specifically, the wavelength at which the reagent absorbs light, is preferably different from the wavelength at which the reacted material absorbs light. This is necessary in order to be able to distinguish the absorption of the reacted product. In the above studies, the LED selected produced a relatively broad emission spectrum with a peak output at about 560 nanometers. The reactants passed therethrough were found to absorb primarily at about 500 nanometers, whereas the reagent absorbed at about 420 nanometers.

An additional advantage of the use of this detector 10 as a dedicated detector for cation chromatography is that by making the detector, particularly the flow cell 17 segment thereof, so small, the fluid dispersion attributed to the flow cell 17 remains quite small. As well known in the chromatography field, minimizing the dispersion of the system is important to maintain good resolution of the chromatographic peaks.

As a consequence of using this detector, it has been found that not only can the different peaks i.e., the different metal elements, be easily and accurately determined, primarily due to the different elution times from the column, but additionally, the elements can be quantitatively analyzed by means of the light absorption detector.

Referring to FIG. 4 a list of metals tested is tabulated along with their absorption maxima and the sensitivity measured. The eight metals are among the most frequently analyzed in the fields of pollution and environmental protection. As aforementioned, and shown in the center column, the metals tested exhibit maximum absorption at about 500 nanometers. The results listed in the third column clearly demonstrate that very low concentrations (i.e. a few parts per billion) of these metals can be successfully determined by use of the detector apparatus 10.

Although the present detector apparatus has been described in an exemplary embodiment other arrangements and configurations are also possible. Consequently, this embodiment is not deemed limiting and the scope and spirit of the present invention is deemed limited only by the appended claims and the reasonable interpretation thereof.

What is claimed is:

1. A dedicated cation detector arrangement for the direct detection of cations, said arrangement comprising:

means for supplying eluted cation effluent for detection of metal cations therein;

a reaction vessel; said vessel being in fluid flow communication with said means for supplying eluted cation effluent;

means for supplying a reagent to said reaction vessel of the type adapted to react therein with said effluent to form a reactant with meal cations having maximum light absorption at approximately a preselected wavelength for direct detection of absorptivity and quantification of metal constituents; and a dedicated light absorption detector assembly for the direct detection of said reactant of cations having a total length of about 23 millimeters; said assembly including a unitary housing having a central axis; said housing having an outside diameter on the order of about 17 millimeters and an opening through the center portion thereof of the order of about 0.74 millimeters; an elongated tubular sample flow cell mounted along said axis substantially in the middle of said housing; said flow cell defining a volume of about 1.7 microliters, said flow cell having an inlet tube directly at one end thereof, which is connected to said reaction vessel for receiving said reactant therefrom, said inlet tube having an inside diameter of about 0.25 millimeters, said inlet tube being disposed at an acute angle with respect to said axis, said flow cell having an outlet tube directly at the other end thereof, which is disposed substantially parallel to said inlet tube; said outlet tube having an inside diameter of about 0.5 millimeters; a first window mounted on said axis in said housing and sealingly connected to one extremity of said flow cell; a light emitting diode integrally mounted in said housing on said axis and being disposed adjacent said first window, said diode having a peak wavelength output of approximately said preselected wavelength of maximum light absorption of said reactant of cations; a second window mounted on said axis in said housing and sealingly connected to the other extremity of said flow cell, said inlet tube being aligned to inlet into said flow cell directly against said second window, a photosensitive detector means for directly detecting absorptivity of metal cation reactant in said flow cell to determine quantification of the respective metal, said detector means being mounted on said axis integrally in said housing and being disposed adjacent said second window; said second window having a convex surface facing said photosensitive detector to disperse a light beam passing through the flow cell onto the total sensitive area of the photosensitive detector.

2. The arrangement of claim 1 wherein said means for supplying reagent comprises a source of reagent connected to said reaction vessel, said reagent being adapted to form a reactant with the separated metal cations having maximum light absorption at approximately said preselected wavelength for direct detection of absorptivity and quantification of metal constituents.

3. The arrangement of claim 2 wherein said reagent is 4-(2-pyridylaza) resorcinol.

4. The arrangement of claim 3 wherein said light emitting diode has a peak wavelength output of approximately 500 nanometers.

* * * * *

UNITED STATES PATENT AND TRADEMARK OFFICE
CERTIFICATE OF CORRECTION

PATENT NO. : 5,073,345
DATED : December 17, 1991
INVENTOR(S) : Raymond P.W. Scott and Gary J. Schmidt It is certified that error appears in the above-identified patent and that said Letters Patent is hereby corrected as shown below:

Column 2, line 54, after "and" insert --held--

Column 3, line 37, delete "14" and insert --17--

Column 4, line 53, delete "meal" and insert --metal--

Signed and Sealed this

Twenty-fifth Day of May, 1993

Attest:

MICHAEL K. KIRK

Attesting Officer

Acting Commissioner of Patents and Trademarks